(12) United States Patent
Ducheyne et al.

(10) Patent No.: US 7,850,994 B1
(45) Date of Patent: Dec. 14, 2010

(54) XEROGEL FILMS FOR THE CONTROLLED RELEASE OF PHARMACEUTICALLY ACTIVE MOLECULES

(75) Inventors: Paul Ducheyne, Rosemont, PA (US); Shulamith Radin, Voorhees, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 205 days.

(21) Appl. No.: 11/403,335

(22) Filed: Aug. 28, 2006

Related U.S. Application Data (60) Provisional application No. 60/675,214, filed on Apr. 27, 2005.

(51) Int. Cl.
  *A61K 9/14* (2006.01)
  *A61F 13/00* (2006.01)
  *A61F 2/00* (2006.01)
(52) U.S. Cl. .................. 424/486; 424/422; 424/424
(58) Field of Classification Search ............... 424/486
See application file for complete search history.

(56) References Cited

U.S. PATENT DOCUMENTS

| | | | | |
|---|---|---|---|---|
| 5,591,453 | A | 1/1997 | Ducheyne et al. | 424/484 |
| 5,817,327 | A | 10/1998 | Ducheyne et al. | |
| 5,830,480 | A | 11/1998 | Ducheyne et al. | 424/400 |
| 5,849,331 | A | 12/1998 | Ducheyne et al. | 424/484 |
| 5,861,176 | A | 1/1999 | Ducheyne et al. | 424/486 |
| 5,871,777 | A | 2/1999 | Ducheyne et al. | 424/486 |
| 5,874,109 | A * | 2/1999 | Ducheyne et al. | 424/486 |
| 5,964,807 | A | 10/1999 | Gan et al. | 623/17 |
| 6,569,442 | B2 | 5/2003 | Gan et al. | 424/426 |

OTHER PUBLICATIONS

Strawbridge et al. (The Factors Affecting the Thickness of Sol-Gel Derived Silica Coatings Prepared by Dipping, Journal of Non-Crystalline Solids 86 (1986) 381-393, printed pp. 1-14) in view of Brinker et al. (Sol-Gel Science, The Physics and Chemistry of Sol-Gel Processing (copyright 1990), printed pp. 1-837).*
Brinker et al. (Sol-Gel Science, The Physics and Chemistry of Sol-Gel Processing (copyright 1990), printed pp. 1-837).*
Aughenbaugh, W., et al., "Silica sol-gel for the controlled release of antibiotics. II. The effect of synthesis parameters on the in vitro release kinetics of vancomycin," *J. Biomed. Mater. Res.*, 2001, 57, 321-326.
Böttcher, H., et al., "Sol—gel composite films with controlled release of biocides," *J. Controlled Release*, 1999, 60, 57-65.
Brinker, et al., "Sol-gel science. The physics and chemistry of sol-gel processing," *Sol—Gel Science—The Physics and Chemistry of Sol—Gell Processing, Academic Press*, 1990, Chapter 13, 787-837.
Cappello, J., et al., "in-situ self-assembling protein polymer gel systems for administration, delivery, and release of drugs," *J. of Controlled Release*, 1998, 53, 105-117.
Falaize, S., et al., "In vitro behavior of silica-based xerogels intended as controlled release carriers," *J. Am. Ceram. Soc.*, 1999, 82(4), 969-976.
Guglielmi, M., et al., "Dependence of thickness on the withdrawal speed of SiO2 and TiO2 coatings obtained by dipping method," *J. Mater. Sci.*, 1992, 27, 5052-5056.
Radin, S., et al., "Silica sol-gel for controlled release of antibiotics. I. Synthesism, characterization, and in in vitro release," *J. Biomed Mater. Res.*, 2001, 57, 313-320.
Strawbridge, I., et al., "The factors affecting the thickness of sol-gel derived silica coatings prepared by dipping," *J. Non-Cryst Solids*, 1986, 86, 381-393.
Cappella et al. "In situ self-assembling protein polymer gel systems for administration, delivery, and release of drugs", Journal of Controlled Release, 53, (1998) 105-117.

* cited by examiner

*Primary Examiner*—Sreeni Padmanabhan
*Assistant Examiner*—Timothy E Betton
(74) *Attorney, Agent, or Firm*—Woodcock Washburn, LLP (57) ABSTRACT

Xerogel films on substrates are provided containing pharmaceutically active compounds. Articles incorporating such films are robust, release active compounds at predictable rates and may provide such release for relatively long periods of time. Orthopedic and trauma uses are indicated along with generalized use in contact with body fluids or as biological implants. Methods for fabrication of such films and devices are provided.

46 Claims, 6 Drawing Sheets

XEROGEL FILMS FOR THE CONTROLLED RELEASE OF PHARMACEUTICALLY ACTIVE MOLECULES

FIELD OF THE INVENTION

This application claims benefit under 35 U.S.C. §119(e) of provisional U.S. patent application No. 60/675,214 filed Apr. 27, 2005. The disclosure of the above-referenced patent application is incorporated herein by reference.

The present invention is directed to the preparation of xerogel films on substrates. The xerogel films of this invention contain a pharmaceutically active molecule or molecules, which molecules are controllably released into body fluids when composites comprising the films on substrate are placed in the body of a patient or into contact with body fluid.

BACKGROUND OF THE INVENTION

Previously, it has been known to prepare certain bulk sol-gel materials for use in orthopedics and in certain other therapeutic regimes. In some cases, pharmaceutically active moieties, such as bone morphogenic protein, antibiotics and other species have been included in such bulk sol-gels. These materials have been proposed for use in the body of patients, e.g. for use in surgery such as spine and other orthopedic surgery as well as for use in drug delivery intracorporeally. The preparation of sol-gels generally as well as sol-gels having pharmaceutically active species in them has been disclosed in a number of U.S. patents, including several assigned to the assignee of this invention. These include U.S. Pat. Nos. 5,874,109; 5,849,331; 5,817,327; 5,861,176; 5,871,777; 5,591,453; 5,830,480; 5,964,807; and 6,569,442. Each of these is incorporated herein by reference in order to set forth a number of ways of preparing sol-gels generally useful to the present invention, especially certain sol-gels having pharmaceuticals included within them.

The foregoing sol-gel bulk materials have been included in tissue engineering devices for spine surgical use and in other products proposed for surgical use. These bulk sol-gel derived materials were produced by a room temperature process that included the formation of acid-catalyzed liquid sols, followed by casting, gelation, ageing and drying. Biomolecules could be mixed into the liquid sols to become encapsulated in the resulting solids, which could be formed into discs or granules. The molecules which were incorporated this way were released in a controlled manner and maintained their biological activity. The sol-gels are acceptably stable for such uses and are known to leach out medicaments from their porous structure over periods of time. They are not physically robust and, overall, cannot be used in relatively thin coatings, however.

One of the foregoing patents, U.S. Pat. No. 5,817,327, describes an surgical implant with a sol-gel derived coating. This coating was made of porous silica glass; biologically active molecules, such as antibiotic, were included. However, the disclosed sol-gel process includes the formation of a liquid sol followed by casting, gelation, aging, and drying—all steps which, while suitable for the manufacture of bulk materials, were not satisfactory for the elaboration of practical medical device coatings or useful films for composites. Moreover, the properties, such as the porosity, displayed by sol-gel derived structures made in this way are not appropriate for use in thin films as part of composite implants and the like. A much lower porosity is needed.

Sol-gels are known per se as are many of the overall chemistries which can be used to prepare them. A convenient work summarizing sol-gel technology is Brinker, et al., *Sol-Gel Science—The Physics and Chemistry of Sol-Gel Processing*, Academic Press, 1990. Chapter 13 of this work, which chapter is specifically incorporated herein by reference, discusses the formation of certain kinds of films from sol-gels, typically, silica based films. The general teachings of Brinker does not provide a practical methodology for preparing the kinds of pharmaceutical delivering and other xerogel films as is desired. In particular, Brinker usually calls for a sintering step, which step is not desirable for use in the preparation of the composites of the present invention. Indeed, Brinker et al. focused on the effects of various processing parameters such as the sol composition (water concentration, alcohol concentration and pH of the sols); the incorporation of biomolecules was never considered. Thus, those authors never appreciated the need to alter processing properties to incorporate desirable quantities of medicaments, factors and other desirable therapeutic molecules in films for subsequent, controlled release—all while maintaining stability and mechanical adhesion to a substrate.

Böttcher et al, Sol gel composite films with controlled release of biocides, J. Controlled Release, vol. 60, page 57-65 (1999) used a sol-gel process for depositing thin films incorporated biocides. These include antimicrobial acids, such as benzoic, ascorbic and boric acids which are used for food and wood preservation. Alcohol solutions of biocides were added to water-free sols which by themselves had a high acid and alcohol content (alcohol/TEOS ratio>4). In a single-step process, the sols were applied to a polymeric foil to form a single-layer film. These one-layer films showed a short-term release: about 90% of the incorporated biocides were released within 10 hours.

The process described by Böttcher suffers from major limitations, and is not acceptable for preparing thin silica sol-gel films for the controlled release of therapeutic biomolecules. Among other things, the processes taught by Böttcher do not allow for using water, as is strongly desired for medicaments. Moreover, the amount of release of molecules is too small for practical use in pharmaceutics. Additionally, the release duration is too short and the adhesion of the films to metallic substrates is unsatisfactory for these purposes.

Risk of infection is considerable in open fractures and its prevention is challenging, especially when fracture fixation material is used. Bacteria can adhere to internal fixation nails that are used to stabilize the fractured bone and form a biofilm. The high resistance of the biofilm to systemic antibiotic treatment can necessitate further surgical procedures. One way to avoid this problem is to use a device that provides a controlled release of antibiotics. Sol-gel derived silica bulk xerogels have been disclosed as materials for the controlled release of antibiotics such as vancomycin. Radin S, Ducheyne P, Kamplain T, Tan B H. Silica sol-gel for the controlled release of antibiotics. I. Synthesis, characterization, and in in vitro release. J Biomed Mater Res 2001; 57:313-20; Aughenbaugh W, Radin S, Ducheyne P. Silica sol-gel for the controlled release of antibiotics. II. The effect of synthesis parameters on the in vitro release kinetics of vancomycin. J Biomed Mater Res 2001; 57:321-26.

These bulk xerogel materials were produced by a room temperature process, which included the formation of acid-catalyzed liquid sols followed by casting, gelation, aging, and drying. The antibiotic incorporated into liquid sols becomes encapsulated into resulting bulk xerogels shaped either as discs or granules. The antibiotic is released from these xerogels in a controlled manner and maintains its bactericidal activity in this bulk form.

There remains a great need for materials useful in surgery, in therapeutics, for the treatment of wounds and otherwise which effect the controlled release of pharmaceutically active molecules. It has long been desired to provide materials, e.g. which are bacteriostatic and can be used in emergent therapy for wounds. Other materials are desired for use in surgery, especially orthopedic surgery while still other uses involving such controlled release of medicaments will find immediate application in diverse therapeutic regimes.

SUMMARY OF THE INVENTION

The present invention provides biocompatible composites for use in contact with body fluids for therapeutic, orthopedic, and other uses. The composites are formed from a sol-gel layer formed on a substrate, the sol-gel layer giving rise to a xerogel film on the substrate. The xerogel contains at least one pharmaceutically active compound by reason of that compound's having been included in the sol-gel layer. It is desired that the xerogel film have a relatively small thickness, preferably from about 0.05 to about 10 µM, with thicknesses from about 0.3 to about 2 µM being preferred and thicknesses from about 0.5 to about 1.5 µM also being preferred.

Sol-gels of the invention may be formed in a number of ways, but are preferably formed by hydrolysis of silicon alkoxide to form a liquid sol in which water or other solvent are mixed. It is convenient for the pharmaceutically active compound to be water miscible or at least significantly soluble to facilitate its inclusion in the sol and, hence in the xerogel films. The sol-gels may be formed by manipulating pH of the solutions forming them, especially by rendering those solutions acidic.

The xerogel films of the invention preferably have porosities of less than about 20 percent, preferably less than about 15 percent. It is also desirable for some embodiments that porosity of the xerogel films be less than 10 percent and even less than 5 percent. As porosity decreases, so does surface area. Thus, it is preferred that surface areas of the xerogel films of the invention be less than about 200 m$^2$/g with figures less than about 150 m$^2$/g being preferred.

The xerogel films of the invention and the biocompatible composites and devices incorporating them contain pharmaceutically active compounds. Compounds suitable for such inclusion may be any or any combination of antibiotic, antineoplastic, antiangiogenic, antithrombogenic, anti-inflammatory, analgesic, a cytokine or a tissue growth stimulating moiety. Indeed, a priori, any compound which can evoke a biological response in a patient or in a tissue may be incorporated in the xerogel films so long as the same is compatible with the chemistries and structures required by the invention. One exemplary pharmaceutical agent which illustrates the present invention is vancomycin. Such compounds may also be naturally occurring molecules whose delivery intracorporeally is beneficial. Examples of these are growth factors and signaling molecules.

The devices of the invention are fabricated by elaborating upon a substrate, starting from a liquid sol, a sol-gel layer containing a pharmaceutically active compound. The sol-gel layer is then allowed to form a xerogel film of diminished thickness through loss of solvent, e.g. water. This process is attended by decrease in porosity of the layer as it forms the film together with reduction in the surface area thereof. The eventual thickness, porosity and surface areas of the xerogels of the invention may be controlled through judicious selection of solvent system, concentration, viscosity and thickness of the elaborated sol-gel layer. Adjustment of the foregoing variables may be performed by one skilled in the art once the present invention is appreciated.

It may be desirable for the sol-gel layer to contain other things beside pharmaceutically active compound. Thus, fibers, filler and a host of material for altering the physicochemical behaviour of the xerogel films may be so included. In one embodiment, particles of the same or of a different sol-gel may be included in the sol-gel layer and either the layer or the particles or both may contain active compounds. The sol-gel layer (and, eventually, the xerogel film) may also contain micro or nano particles which may, in turn, confer beneficial properties. For example, inclusion of liposomes containing a drug or bioactive molecule may confer effective behavior upon devices made of xerogel films containing them. Such micro and nano structures are known per se and their inclusion is within the ordinary skill of the routineer.

Multi layer assemblies having a plurality of xerogel films or of one or more xerogel films together with other layers or films on a substrate may also be prepared in accordance with this invention. Thus, for example, serial application of sol-gel layers on a substrate with subsequent removal of solvent may give rise to such multi layer articles. Each film of the article can contain the same or a different pharmaceutically active compound or, indeed, may contain no biologically active material at all.

The xerogel films of the present invention may be characterized in several alternative ways. From a physical point of view, the desired xerogels have a relatively thin thickness as compared to prior pharmaceutical eluting films. Thus, xerogel films in accordance with the invention can be characterized as having thicknesses of from about 0.05 µM to about 10 µM. Preferably, the films have a thickness between about 0.2 µM to about 5 µM, with thickness between about 0.5 µM to about 1.5 µM being preferred for some embodiments.

The xerogel films may also be characterized by porosity. Porosity is expressed in percent and will be appreciated as being the ratio of void to xerogel material expressed as a percentage. Porosity can be measured in a number of ways, however for the purposes of this invention, porosity should be measured by determination of the refractory index or by B.E.T. analysis, such as performed by S. Falaize, S. Radin and P. Ducheyne, In vitro behavior of silica-based xerogels intended as controlled release carriers, J. Am. Ceram. Soc., 82, 969-976 (1999)

It is preferred that the xerogel films of this invention have a porosity less than 20 percent, with porosities less than about 15% being preferred and less than 10% also being preferred for some embodiments. Lesser porosities may also be utile when consideration is given to the overall objectives for the xerogels of this invention.

A further characterization of the xerogels of the present invention is in terms of their specific surface area. As will be appreciated, surface area generally is related to porosity. In the invention, surface areas are to be measured by using the same B.E.T. technique. Specific surface areas are between about 25 and 250 m$^2$/g, with surface areas between 50 and 200 m$^2$/g being preferred and 75 and 150 m$^2$/g being preferred for some embodiments.

It will be appreciated that the systems for elaborating sol-gel layers, ensuing xerogel films and devices incorporating such films include complex chemical and other relationships. Thus, the substrate and sol solution are best described by how they relate to each other and how the film, once formed, may be converted into xerogel films having desired properties. Thus, the substrate should be one which is compatible with the sol-gel material. Generally, this requires that it be wettable by the sol-gel and that it not chemically react therewith.

Glasses, ceramics, metals and many plastic and rubber materials may be used as substrates for this process, with metallic substrates being preferred for many embodiments. The sol-gels for use herein are compatible with the selected substrate and have chemistries which do not negatively interact either with a patient, when an ensuing xerogel is implanted or used in contact with body fluid, or with the pharmaceutically active compound to be included therein. The sol-gels must also be comprised of a solvent which can be removed so as to form the desired xerogel having some or all of the desired thickness, porosity and surface area.

Conveniently, this is achieved by making a liquid sol containing water and other solvents miscible with water such as alcohols and water soluble biological agents. Solutions containing some alcohol may be useful, however it is generally not necessary for the sol-gels to comprise a predominant amount of alcohol. Some alcohol is preferred to reduce the viscosity, but the water is typically essential as most drugs or molecules are soluble in water.

The concentrations of components and viscosity of the solutions or suspensions from which the sol-gel layers are to be formed may be adjusted, chiefly by adjusting solvent concentrations, to provide sol-gel films which yield xerogel films with the desired properties.

Xerogel films are achieved by removing solvent from sol-gel layers on substrates. This may be done through simple drying, by desiccation or by application of heat and/or vacuum. The properties of the resulting xerogel films will serve as a guide to persons skilled in the art who will readily appreciate how to vary such conditions to achieve them.

The general chemistries and methodologies for preparing sol-gels which may be used to good effect in connection with certain embodiments of the present invention are known to persons of skill in the art. The patents and reference set forth in the background section of this disclosure, provide an effective overview of such principles and they will not be repeated here. All are, however, incorporated in this specification to provide such background as may be necessary for the routineer to achieve the preparation of useful sol-gels. The elaboration of films from the sol may be accomplished by any convenient technique including dipping, employment of a doctor blade, spinning and otherwise. Solvent removal may similarly be achieved by simple drying or by applying heat or vacuum. The heat, however, should not lead to degradation of the biological function of the incorporated molecule. In some cases, precipitation of sol-gels with dissimilar solvents generally in the way that ultrafiltration membranes are formed may also be employed so long as the degree of porosity is acceptable for the article to be so formed.

It has now been found that implantable and other devices having xerogel films containing pharmaceutically active compounds in accordance with this invention release those compounds in a predictable and highly desirable way. Thus, rather than delivery of active compound from the pores of a highly porous material, the present articles deliver pharmaceutically active compound from the material itself. While not wishing to be bound by theory, it is not clear whether active compound delivery occurs through surface dissolution of the compound from the xerogel material over time or whether physical ablation of the xerogel material liberates the active compound. Indeed, another mechanism may be effective in achieving this result. In any event, stable, predictable and selectably variable delivery of such compounds may now be achieved.

The advantages to human and animal therapeutics are significant. By now being able to deliver, e.g. drugs at a steady rate over many months' time, the employment of eluting devices, e.g. stents, implants and the like, may be had for contexts far beyond those presently possible using prior technologies. When multiple layers of xerogels are employed on substrates, either longer term deliveries of pharmaceutically active compound may be achieved, differing levels of release may be had, sequential delivery of different drugs or drug combinations may be attained, or combinations of the foregoing.

Articles having such plural films of xerogels may be attained through this invention in very straightforward ways. Once an initial xerogel film has been satisfactorily elaborated upon a substrate, a further sol-gel layer, which may have either the same or a different composition from the sol-gel giving rise to the first xerogel film, is placed upon the first film. Solvent is removed, thus forming the second film. This may be repeated. For some embodiments, one film is prepared for application of a successive film by treating it for 2 to 5 minutes in surface conditioning solution such as a phosphate buffered saline (PBS, pH 7.4, Gibco)

It has been found that the articles provided by this invention feature xerogel films which have excellent mechanical adhesion to the substrates, especially to metal substrates. This stability is highly beneficial for implantation in patients. Even very thin films of xerogels release useful amounts of pharmaceutically active material into body fluids and the release kinetics are believed to be stable and predictable. Concomitantly, a relatively long release profile, on the order of weeks or months, may be attained, making the present articles flexible and useful for long term therapy.

BRIEF DESCRIPTION OF THE DRAWINGS

FIGS. 1 *a*, b. Weight of single-layer coatings (W/cm2) without (1*a*) and with vancomycin (1*b*) as a function of sol dilution (R2 and R2.5) and withdrawal speed.

FIGS. 2 *a,b*. The effect of sol dilution (Eth/TEOS ratio, R) on the weight of vancomycin-free coatings (2*a*, upper figure) and on the vancomycin load (µg/cm2) in coatings with 10 and 20% vancomycin concentrations (2*b*, lower figure).

FIGS. 3 *a,b*. Mean cumulative vancomycin release (3*a*) and degradation (weight loss) (3*b*) of single-layer R2.5 coatings as a function of vancomycin concentration (0, 10 and 20%) and immersion time.

FIGS. 6 *a,b*. Mean cumulative vancomycin release (a) and the film degradation (weight loss) (b) versus vancomycin concentration in the film composed of three layers. The error bars represent the standard deviation (n=3).

FURTHER DISCLOSURE AND NON-LIMITING EXAMPLES

Thin Xerogel Films on Fracture Fixation Materials

Antibiotic-loaded xerogel films are produced by applying a liquid sol with an incorporated drug on a metallic substrate. It was believed that certain properties of thin sol-gel derived silica films depend on the sol composition and the withdrawal speed. The effect of these parameters on the properties of antibiotic-loaded xerogel films and the controlled release of vancomycin from thin xerogel films on a Ti-6Al-4V substrate were determined.

Ti-6A-4V strips (ELI grade, President Ti), 0.5 mm thick and 21 mm wide, were used for the coating deposition. The strips were cut into 25 mm-long samples. The samples were cleaned (first, in acetone for 30 minutes and then in 2% detergent for 1 hour), rinsed with deionized (DI) water and then passivated in 35% nitric acid for 1 hour. After passivation, the samples were thoroughly rinsed with DI water and then dried in a laminar flow hood located in a clean room. The samples were kept in the hood until application of the coatings.

Sols derived from acid-catalyzed tetraethylorthosilane (TEOS) and diluted with ethanol were used for elaboration of thin, crack-free coatings. TEOS, DI water and 1N HCl (DI:HCl:TEOS=5:0.01:1) were mixed in a glass beaker and stirred using a magnetic stirrer to form a sol. Then, various amounts of ethanol (Eth) were added to the sol to produce various Eth:TEOS volume ratios (R) varying from 1.5 to 2.5. The sols were kept in sealed glass containers. Although acid-catalysed sols diluted with ethanol are stable for several weeks, only freshly made sols were used for the deposition of coatings.

Vancomycin is a water-soluble drug. Sols with nominal vancomycin (Vancomycin-HCL, NovaPlus) concentrations of 5, 10, and 20% by weight were made by adding corresponding amounts of vancomycin dissolved in DI water to the sol. Although sols with various vancomycin concentrations were stable for several days, only freshly prepared mixtures were used for the application of the coatings.

Dipping can be used for the deposition of sol-gel derived coatings onto various substrates. It is well known that the coating properties such as thickness and integrity depend on the sol composition and the withdrawal speed. A dipping device with a well-controlled withdrawal speed was used for the coating deposition. The device is composed of a stepping motor with a controlled screw-driven, vertically mounted gliding unit (UniSlide, Velmex, Inc., East Bloomfield, N.Y.). For the deposition of sols, the withdrawal speeds varied in a range from 50 to 100 mm/min. After deposition, the coatings were dried in a laminar flow hood in a clean room. In order to produce certain coatings composed of several layers, the dipping and drying procedures were repeated several times.

Morphology of the coatings was observed by using optical microscopy (at magnifications up to ×400) in combination with a high resolution video camera. Coating weight were measured with the use of a Sartorius balance with readability of 0.01 mg. The thicknesses of the coatings were measured by ellipsometry. As ideally smooth surface is required for the precise measurements of the thickness of thin films, the coatings were applied on silicon wafers. Standard procedure was applied to clean and modify the surface of the wafers. The thickness of sol-gel films were measured as a function of the withdrawal speed and sol composition.

Both degradation and elution studies were conducted in phosphate buffered saline (PBS, pH 7.4, Gibco) with daily solution exchange. Degradation of the coatings was monitored by measuring the weight loss as a function of immersion time. Concentrations of released vancomyicn were measured spectrophotometrically (Ultraspec Plus UV/vis spectrophotometer) at 280 nm. Known concentrations of vancomycin in PBS were used as standard solutions.

The Effect of Processing Parameters on the Physical Properties of a Single-Layer Film The thickness of sol-gel derived films produced by one-step dipping process can be varied by either varying the sol dilution with a solvent (such as alcohols) or by varying the withdrawal speed. Ti-6Al-4V strips, 0.5-mm thick and 21-mm wide, were used for deposition of a thin xerogel film. The strips were cut into 25-mm long samples. Prior to film deposition, the samples were cleaned (first, in acetone and then in 2% Liqui-Nox detergent) and passivated. TEOS-derived sols used for this experiment were prepared as follows: TEOS, water and 1N HCl were mixed at the $H_2O$:TEOS:HCl ratio=5:1:0.01 and stirred for 2 hours. Then the sols were diluted with ethanol at Eth/TEOS volume ratios varying from 1 to 2.5. Vancomycin concentrations in the sols were 0, 10, and 20% by weight. One-step deposition process by dipping was used to obtain a xerogel film composed of one layer. Withdrawal speed varied in the range from 50 to 300 mm/min. Prior to sol deposition, corresponding amounts of vancomycin solution in water were added to the sol.

Tables 1 and 2 show the effects of sol dilution with ethanol (Eth/TEOS ratio, R) and withdrawal speed on the thickness and integrity of vancomycin-free films deposited on silicon wafers. The data demonstrate the coating thickness increases with a decrease of R or with an increase of withdrawal speed. These observations correspond to the literature data. Brinker C J, Scherer G W. Sol-gel science. The physics and chemistry of sol-gel processing. San Diego, Calif.: Academic Press, 1990, Ch. 13, p. 787-838; Gugliemi M, Colombo P, Peron F, Mancinelli Degli Espoti L. Dependence of thickness on the withdrawal speed for SiO2 and TiO2 coatings obtained by dipping method. J Mater Sci 1992; 27:5052. Observed, thicker coatings, which are applied from sols with dilution ratio R equal or below 1.5 are prone to cracking. The use of withdrawal speeds greater than 250 mm/min for R2 sols also leads to cracking. See also Strawbridge I, James P F. The factors affecting the thickness of sol-gel derived silica coatings prepared by dipping. J Non-Cryst Solids 1986; 86:381-393. Bottcher H, Jagota C, Trepte J, Kallies K-H, Haufe H. Sol-gel composite films with controlled release of biocides. J Control Release 1999; 60:57-65.

TABLE 1

Properties of sol-gel film vs. sol dilution with ethanol (Eth/TEOS volume ratio, R)

| Eth/TEOS Ratio | d of sol g/cm³ | Thickness μm | Film integrity (optical microscopy) |
| --- | --- | --- | --- |
| 1.0 | 0.94 | >0.5 | flaky, grainy, comes off |
| 1.5 | 0.92 | 0.30 | large cracks |
| 2.0 | 0.89 | 0.20 | thin, uniform, crack-free |
| 2.5 | 0.85 | 0.18 | thin, uniform, crack-free |

Note:
Coatings were deposited on silicon wafers at withdrawal speed of 100 mm/min.

TABLE 2

Properties of R2 sol-gel films on Si wafers vs. withdrawal speed

| Withdrawal speed mm/min | Thickness μm | Film integrity (optical microscopy) |
| --- | --- | --- |
| 50 | 0.17 | crack-free, uniform |
| 100 | 0.20 | crack-free, uniform |
| 150 | 0.22 | crack-free, uniform |
| 300 | 0.26 | large cracks |

Figure 1A:
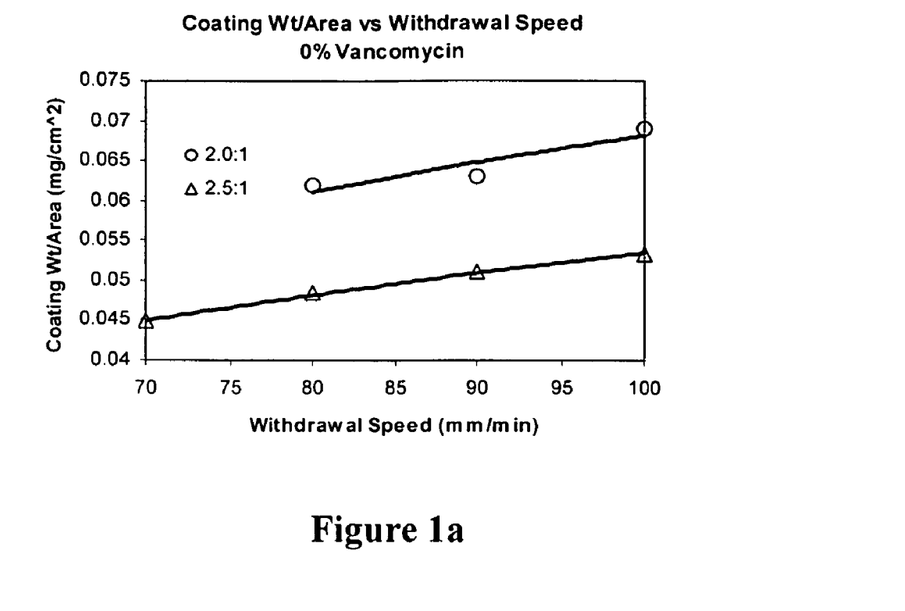
Figure 1B:
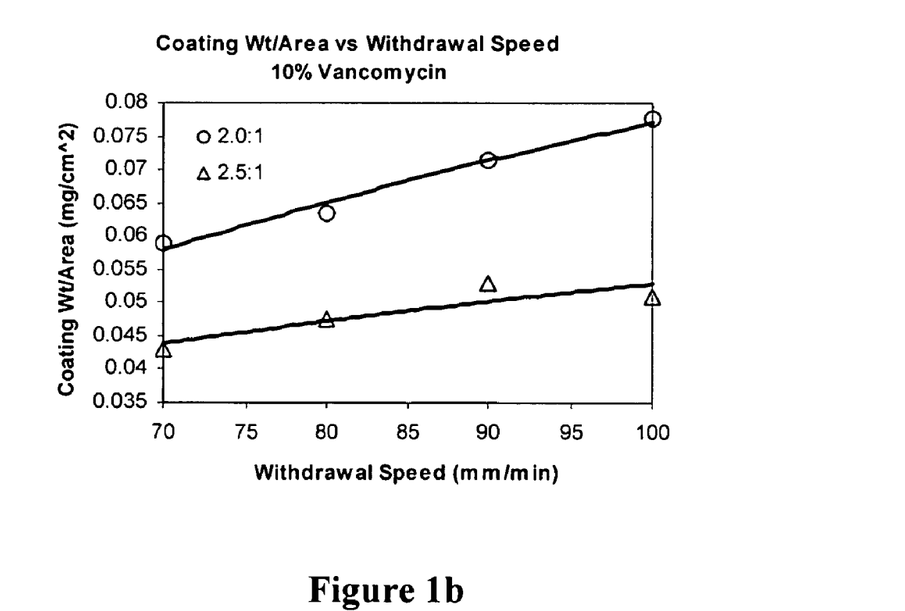

FIGS. 1a and 1b show the effect of withdrawal speed (varying in the range from 70 to 100 mm/min) on the weight (W, mg/cm2) of coatings, either with or without vancomycin, deposited from R2 and R2.5 sols. Both vancomycin-free (FIG. 1a) and vancomycin-containing coatings (FIG. 1b) showed a linear increase in the weight with increasing speed. Concerning the effect of R, the weight of coatings deposited from R2 sols was about 50% greater than that of coatings deposited from R 2.5 sols.

Figure 2A:
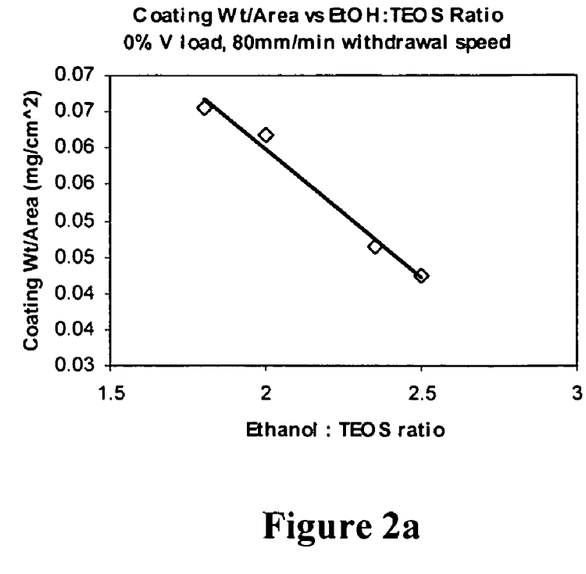
Figure 2B:
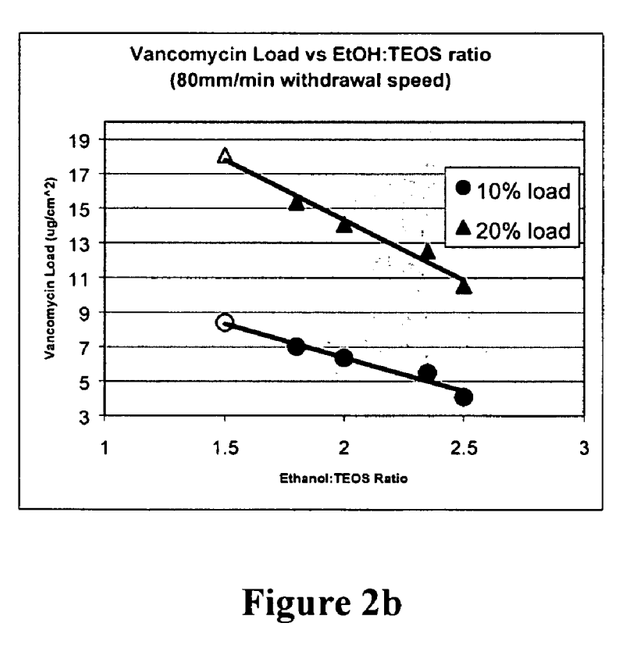

FIGS. 2a and 2b illustrate the effect of R varying in the range from 1.5 to 2.5 on the weight of vancomycin-free coatings (FIG. 2a) and on the vancomycin load of the coatings containing 10 and 20% of vancomycin (FIG. 2b). The data show a linear increase in the weight of coatings with a decrease of R from 2.5 to 1.5. In fact, in comparison to R2.5 coatings, the 1.5R coatings showed a 2-fold increase in the weight. As shown in FIG. 2b, the increase in the vancomycin load corresponds to the increase in weight. Almost a double increase in the vancomycin load can be achieved by decreasing the R value from 2.5 to 1.5. However, as shown above (Table 1), the R1.5 coating, either without or with vancomycin, are prone to cracking during drying.

The data in Tables 1 and 2 and in FIGS. 1 and 2 show that the thickness of silica xerogel film produced by a one-step deposition process can be increased by either decreasing the sol dilution with ethanol (Eth/TEOS ratio or R) or by increasing the withdrawal speed. The effect of these parameters on the vancomycin load in the film was similar (FIG. 2b). The data also demonstrate that the increase in the thickness and the load is limited as films thicker than 0.25 μm showed multiple cracking.

These results suggest that a significant increase in the film thickness and corresponding increase in the load can hardly be achieved by using a one-step deposition process as the increase in thickness above 0.25 μM leads to the film cracking.

Crack-free vancomycin-loaded xerogel coatings can preferably be obtained by using sols with R equal or greater than 2 and withdrawal speeds in a range 80-100 mm/min.

In Vitro Stability and Vancomycin Release from Single-Layer Sol-Gel Coatings

Figure 3A:
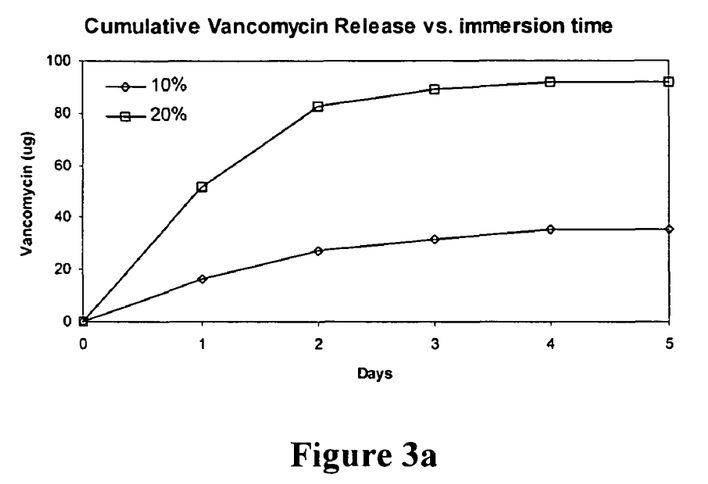
Figure 3B:
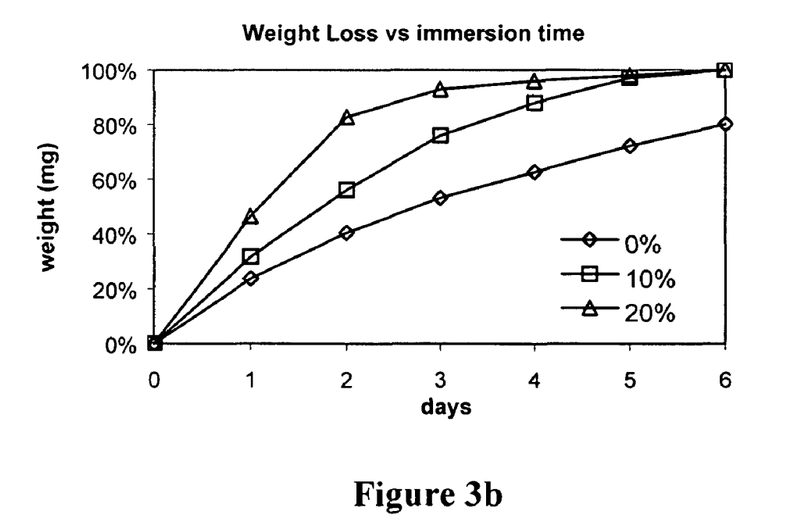

Coatings deposited from R2 and R2.5 sols at withdrawal speed of 80 mm/min were used for the following examples. Nominal vancomycin concentrations in both R2 and R2.5 coatings were of 0, 10, and 20%. FIGS. 3a and 3b illustrate the effect of increasing vancomycin concentration on the release (FIG. 3a) and degradation (FIG. 3b) properties of R2.5 coatings.

As shown in FIG. 3a, the coatings showed a time- and load-dependent release. The rate of release and the total amount released from coatings with 20% vancomycin were significantly greater than those from coatings with 10% vancomycin. At both 10 and 20% concentration, the initial faster release with subsequent slower release was observed. For both concentrations, about 80% of the original vancomycin load was released after two days of immersion. The effect of vancomycin concentration on the release properties of R2 coatings was similar. The degradation of the coatings was assessed by measuring the weight loss as a function of immersion time. The data in FIG. 3b show that incorporation of vancomycin in the coatings affects their stability. Vancomycin-free coatings showed weight loss about 80% after 6 days of immersion. In comparison, for coatings containing 10 and 20% of vancomycin 80% weight loss occurred by day 2 and day 3, respectively.

The effects of sol dilution and vancomycin concentrations on the original vancomycin load (μg/cm$^2$), the initial release rate (μg/cm$^2$/d), the time to 80% release of the original load and to 80% of coating dissolution (80% weight loss) are summarized in Table 3. These data suggest that the use of R2 sols allows to increase the vancomycin load in the coatings. At larger vancomycin concentrations, an additional increase of the load and release rates can be achieved. The initial daily release from coatings R2 and R2.5 coatings with 10% vancomycin were 1.2 and 1.3 μg/cm$^2$, respectively. This daily release was below the Minimal Inhibitory Concentration (MIC) of vancomycin against *Staphylococcus aureus* (1.5-3 μg/ml). In comparison, the initial daily release from the coatings with 20% vancomycin (3.5 and 4.7 μg/cm$^2$ for R2 and R2.5 coatings) exceeded the MIC. However, with 80% of release by day 2, the daily release was significantly reduced. Further increase of the vancomycin load and of the daily could be achieved with the use of coatings composed of several layers.

TABLE 3

The effect of sol dissolution (Eth/TEOS ratio, R) and vancomycin concentration on the vancomycin load (μg/cm$^2$), the initial release rate and the time to 80% release of the original vancomycin load and 80% of coating dissolution (weight loss, %).

| R | Concentration % | Load μg/cm2 | Release rate μg/cm2/d | Time to 80% release days | Time to 80% dissolution days |
|---|---|---|---|---|---|
| 2.0 | 0 | — | — | — | >6 |
|  | 10 | 6.5 | 1.2 | 3 | 3 |
|  | 20 | 14 | 3.5 | 2 | 2 |
| 2.5 | 0 | — | — | — | >6 |
|  | 10 | 4 | 1.3 | 3 | 3 |
|  | 20 | 11 | 4.7 | 2 | 2 |

Multi-Step Process for Depositing a Controlled Release Thin Film Composed of Several Layers to Achieve a High Original Vancomycin Load TEOS-derived sols were prepared by mixing TEOS, water and 1N HCl at the TEOS:H$_2$O:HCl=1:5:0.1. The sols were diluted with ethanol at Eth/TEOS volume ratio of 2 and deposited at withdrawal speed 100 mm/min. After depositing the first layer, the attempt to repeat the deposition process failed to produce a uniform second layer. Instead, a network of gelled droplets was observed. Various procedures were tried to improve the quality of the second layer. As a result, it was found that conditioning of the silica films in Na-containing solutions with pH varying from neutral to basic allows for a successive deposition of uniform layers. In further multi-step deposition experiments short-term (3-5 minutes) immersion in phosphate buffered saline (PBS, pH 7.4) was used as the conditioning treatment.

Effect of Number of Layers on the Film Thickness (Weight) and Vancomycin Load

Figure 4:
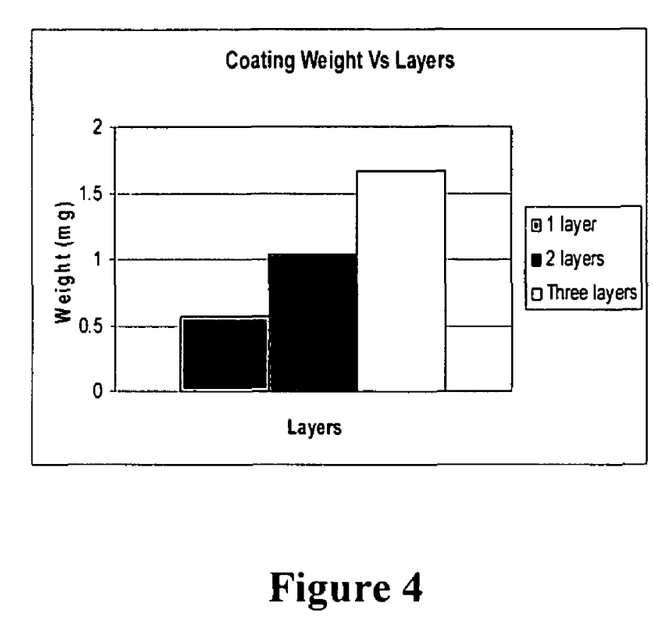
FIG. 4. Weight of coatings composed of one, two or three layers. R 2 sols with and withdrawal speed of 80 mm/min were used for the coating deposition.

Ti-6Al-4V samples, cleaned and passivated, were used for the film deposition. TEOS-derived sols were prepared by mixing TEOS, water and 1N HCl at the TEOS:H$_2$O:HCl=1:5:0.1. The sols were diluted with ethanol at Eth/TEOS volume ratio of 2 and deposited at the withdrawal speed of 100 mm/min. Vancomycin concentrations in the sols were 0, 3, 5, 10, and 20%. Films composed of one or three layers were applied on the Ti-6Al-4V substrate. In order to obtain successive uniform layers, conditioning treatment was performed as described in the previous example. The effects of a number of layers on the weight of coatings and on the vancomycin load are shown in FIG. 4 and in Table 4, respectively.

TABLE 4

Vancomycin Load vs. Number of Layers and Vancomycin Concentration

| Vancomycin concentration | Vancomycin load, μg/cm2 | |
|---|---|---|
| % by weight | 11-coat | 31-coat |
| 3 | 2 | 5 |
| 5 | 3 | 8 |
| 10 | 6 | 17 |
| 20 | 12 | 35 |

FIG. 4 shows the effect of a number of layers on the total weight of coatings. Coatings used for this study were deposited from R2 sols at withdrawal speed of 80 mm/min The increase in the total weight of coatings composed of several layers was practically proportional to the number of layers. In comparison to the weight of a single-layer coating, the coating composed of three layers showed a three-fold increase. As shown in Table 4, vancomycin load also increases with a number of layers. In comparison to single-layer coatings with various vancomycin concentrations, three-fold increase of the load was observed in coatings composed of three layers.

The Effect of Number of Layers on the Vancomycin Release In Vitro

Ti-6Al-4V samples, cleaned and passivated, were used for the film deposition. TEOS-derived sols were prepared by mixing TEOS, water and 1N HCl at the TEOS:$H_2O$:HCl=1:5:0.1. The sols were diluted with ethanol at Eth/TEOS volume ratio of 2 and deposited at the withdrawal speed of 100 mm/min. Vancomycin concentrations in the sols was 10% by weight. Films composed of one or three layers were applied on the Ti-6Al-4V substrate. In order to obtain successive uniform layers, conditioning treatment was performed as described in the prior examples.

Figure 5:
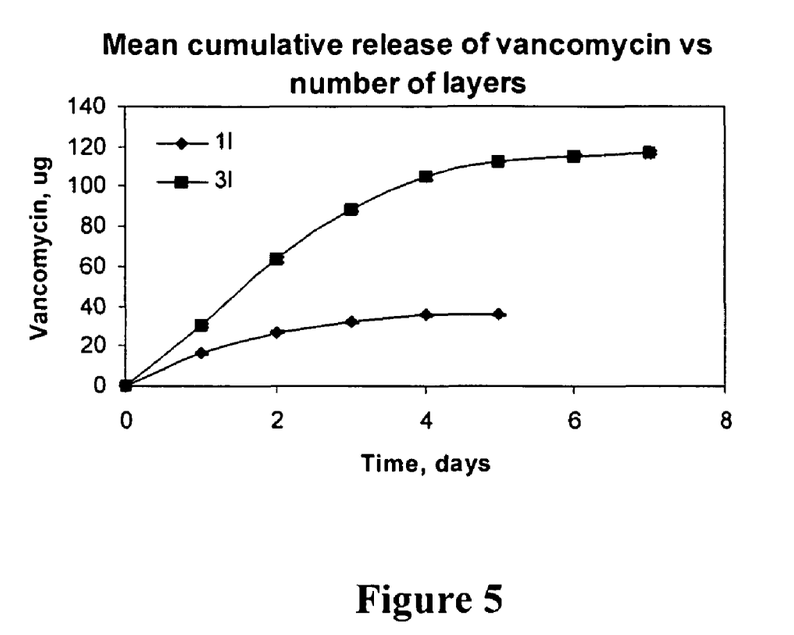
FIG. 5. Mean cumulative release of vancomycin from films composed of one or three layers. Vancomycin concentration in the films was 10% by weight. The error bars represent the standard deviation (n=3). These error bars are barely visible.

Elution experiments were performed in phosphate buffered saline (PBS, pH 7.4) with daily solution exchange. Vancomycin concentrations were measured spectrophotometrically at 280 nm. The studies were conducted in triplicate. The results in FIG. 5 demonstrate that the rate of release, the amount released and the time to total release increased with the number of layers. In comparison to one layer film, there was a 3-fold increase in the amount released from the film composed of three layers. Also, 80% of the original load was released from one-layer film by 2 days. In contrast, the time to 80% release was extended up to 6 days in the case of films composed of three layers.

Effect of Vancomycin Concentration on Release and Film Stability In Vitro

Ti-6Al-4V samples, cleaned and passivated, were used for the film deposition. TEOS-derived sols were prepared by mixing TEOS, water and 1N HCl at the TEOS:$H_2O$:HCl=1:5:0.1. The sols were diluted with ethanol at Ethanol/TEOS volume ratio of 2 and deposited at the withdrawal speed of 80 mm/min. Vancomycin concentrations in the sols were 0, 5, 10, and 20% by weight. Films composed of three layers were applied on the Ti-6Al-4V substrate. In order to obtain successive uniform layers, conditioning treatment was performed as described in the previous examples.

Figure 6A:
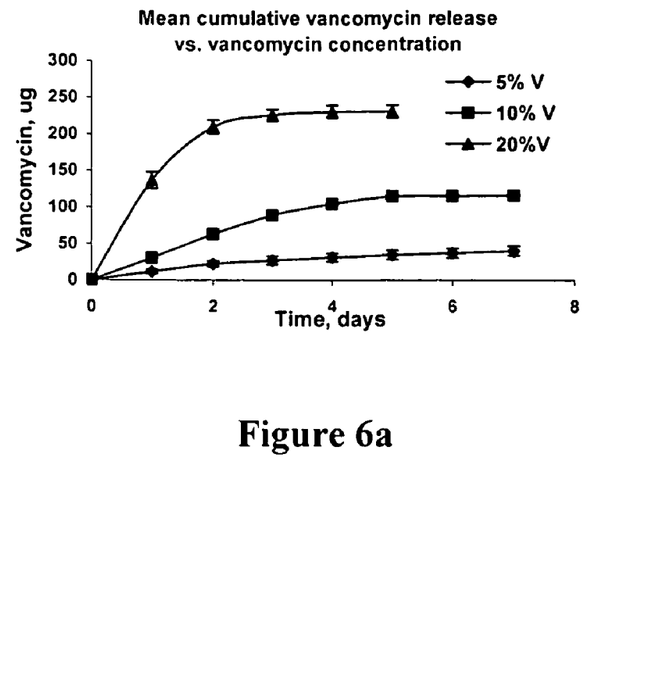

Elution and degradation experiments were performed in phosphate buffered saline (PBS, pH 7.4) with daily solution exchange. Degradation of the coating was monitored by weight loss measurements. Vancomycin concentrations were measured spectrophotometrically at 280 nm. The studies were conducted in triplicate. As shown in FIG. 6a, time- and load-dependent release of vancomycin from the film was observed. The rates of release increased with increasing vancomycin concentration. At higher vancomycin concentration (20%), there was a fast initial release. As a result, 90% of the original vancomycin load was released after two days of immersion. In comparison, slow and linear release was observed at lower concentrations (5%). Only 56% of the original load was released by 7 days of immersion. The daily release of vancomycin exceeded the Minimal Inhibitory Concentration (MIC) of vancomycin against Staphylococcus aureus (1.5-3 12 μm/ml).

Figure 6B:
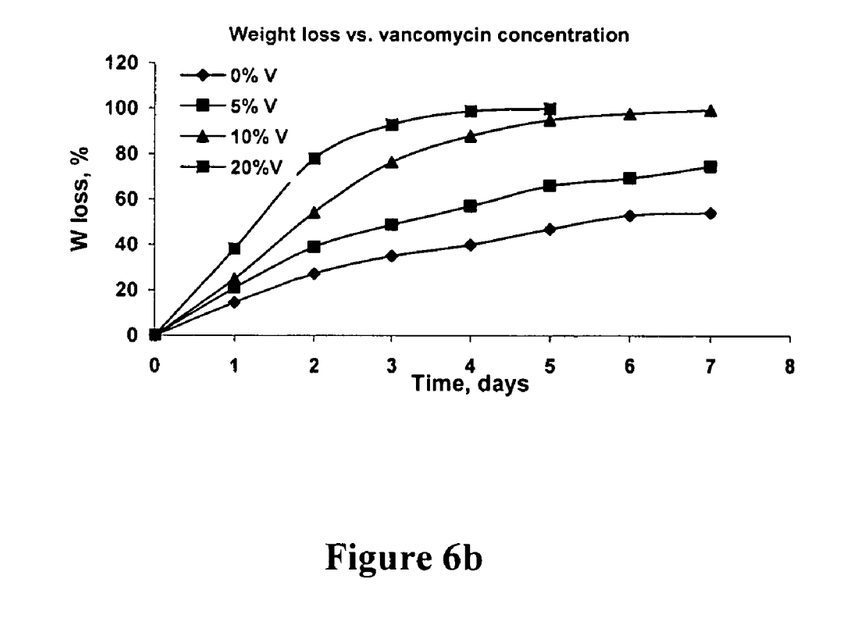

The data in FIGS. 6 a,b demonstrate that both the film stability and the release kinetics were affected by the presence of incorporated vancomycin. As vancomycin concentration in the film increased from 0% to 20%, both the degradation rates (measured as the weight loss of the coatings) and the vancomycin release rates increased. Whereas vancomycin-free films showed only 50% weight loss by 7 days of immersion, films with 20% vancomycin were completely dissolved by 4 days.

FIG. 6a shows vancomycin release from R2 coatings composed of three layers as a function of the drug concentration and immersion time. In comparison to the release properties of single-layer coatings (FIG. 3a), more gradual release over longer period of time was observed. For the coatings with 5% concentration, the initial release with the rate of 10 μg/d was followed by release with a practically constant rate of 5 μg/d. Only 56% of the original vancomycin load was released from these coatings after seven days of immersion. By this time, about 60% of these coatings was dissolved. Coating with larger, 10% concentration showed much faster release with initial release rate of 30 μg/d.

In comparison to a single-layer coating with 10% concentration (FIG. 3a), the 10% coating composed of three layers showed a remarkable improvement (FIG. 6a). A significant increase in the release rates and the total amounts released was observed. In addition, the time to 80% release was extended from 2 days (for one layer) to 5 days (for three layers). Concerning the release rate, single layer coatings showed the initial rate of 1.2 μg/cm$^2$/d, which was below the MIC (Table 3). When three layers were applied, the initial release rate increased to the value of 3.5 μg/cm$^2$/d exceeding the MIC.

FIG. 6b illustrates the effect of incorporated vancomycin on the film stability in vitro. The rates of degradation (weight loss) increased with increasing concentration. Whereas the weight loss of vancomycin-free coating was about 50% by 7 days of immersion, the film with 20% vancomycin was totally dissolved by 5 days.

These in vitro data demonstrate that the thin xerogel films with long-term time-dependent properties can be applied to Ti alloy substrates. Based on the study of the effects of processing parameters, it can be suggested that the release and degradation rates of these coatings can be controlled by varying either the thickness (weight) of the coatings or the vancomycin concentrations, or both.

Adhesion of Vancomycin-Loaded Thin Xerogel Film to a Metallic Surface

Ti-6Al-4V Kirschner anodized wires, 1.2-mm diameter, were used for the adhesion test of the vancomycin-loaded thin xerogel film. The wires were cut into 30-mm long samples. The samples were cleaned, first, in acetone and then in a 2% Liqui-Nox solution, rinsed with deionized water and dried. TEOS-derived sol were prepared my mixing TEOS, water and 1N HCl at the TEOS:$H_2O$:HCl=1:5:0.1. The sols were diluted with ethanol at Ethanol/TEOS volume ratio of 2 and deposited at the withdrawal speed of 80 mm/min. Vancomycin concentration in the sol was 10% by weight. Films composed of five layers were applied on the wire surface. In order to obtain successive uniform layers, conditioning treatment was performed as described in previous examples. Five wire samples with applied film were prepared for the test. The absence of cracking in the films was confirmed with the use of optical microscopy.

The film adhesion was evaluated via press-fit test. Sham surgery was performed using cadaver rat femora. Each of the coated samples was inserted into the medullary channel of the femur through a hole created in the knee. 18G-needle was used to create the hole. The test included push-in and push-out steps. After the test, the samples were rinsed with water, dried and subjected to morphological observations. All samples tested did not show any evidence of cracking.

Attempted Synthesis of Thin Xerogel Film Using the Sol-Gel Process of U.S. Pat. No. 5,817,327

U.S. Pat. No. 5,817,327 describes an implant with a sol-gel derived coating composed of porous silica glass and incorporated biomolecules. The sol-gel process as described in Examples (Example 1, 5 and others) is suitable for manufacturing bulk sol-gel materials. However, it is not satisfactory for processing of thin sol-gel films. The disclosed process included the formation of a liquid sol with incorporated biomolecules followed by casting, gelling, aging, and drying at room temperature, all steps which are typical for processing of bulk sol-gels. Unlike bulk materials, processing steps of thin sol-gel films include the formation of a liquid sol followed by film deposition. At this deposition step, all stages of sol-gel transformation such as gelation, condensation, and drying overlap and occur at once. Resulting sol-gel material is denser that the bulk sol-gels and could be practically nonporous.

Sol preparation described in U.S. Pat. No. 5,817,327 (mixing tetramethylorthosilicate (TMOS, $Si(OCH_3)_4$), methanol, water and acid (1N HCl) at methanol/TMOS ratio of 1 and $H_2O$/TMOS ratio of 10) is not suitable for thin film deposition. Resulting sols are too dense (d=1.05 g/cm$^3$) and too viscous to produce crack-free films or films with a uniform thickness, as we determined experimentally. In addition, TMOS-derived sols were not useful for thin film deposition in the context of this example.

Brinker & Sherer, *Sol-Gel Science—The Physics and Chemistry of Sol-Gel Processing*, Academic Press, 1990, summarize the literature and describe a sol gel process for depositing thin silica films. Liquid sols are applied to a substrate by dipping or spinning. Typically, the process includes acid-catalyzed hydrolysis of a silica precursor such as tetraethylorthosilane (TEOS, $Si(OC_2H_5)_4$) to produce a liquid sol. These sols usually contain little water and are diluted with solvents such as alcohol to obtain a viscosity suitable for film deposition by dipping.

Attempted Synthesis of Thin Xerogel Film with Incorporated Pharmaceutically Active Compound Using Böttcher et al. Sol-Gel Process Böttcher et al used a sol-gel process for depositing thin films. These films incorporated biocides (antimicrobial acids, such as benzoic, sorbic and boric acids which are used for food and wood preservation). Alcohol solutions of biocides were added to water-free sols which by themselves had a high acid and alcohol content (alcohol/TEOS ratio>4). In a single-step process, the sols were applied to a polymeric foil to form a single-layer film. These films showed a short-term release: about 90% of the incorporated biocides were released within 10 hours. Since most of pharmaceutically active agents including antibiotics are soluble in water and not soluble in alcohols, they cannot be incorporated into Böttcher et al sols which do not contain any water.

At the attempt to add a water solution of vancomycin to a sol prepared as described by Böttcher et al, immediate precipitation of the drug in the sol was observed. Modification of the process of sol preparation was required to avoid the precipitation. It was achieved by adding water at the TEOS hydrolysis step. When the $H_2O$/TEOS was equal or above 5, incorporation of even large amounts of vancomycin (up to 30%) to the sol did not produce any precipitation. The sols with vancomycin concentrations varying from 3 to 30% by weight were stable over several days. The sols of modified compositions were successfully used for depositing vancomycin-loaded thin xerogel films to a Ti alloy substrate.

Another limitation of the Böttcher et al process is its one-step deposition process. The amount of a bioactive molecule, which could be incorporated into the resulting one-layer film, is not sufficient for a long-term controlled release. It was found that only a limited amount of vancomycin could be loaded into a one-layer film resulting from the one-step deposition process. The vancomycin load did not significantly exceed the minimal inhibitory concentration (MIC) of vancomycin against *Staphylococcus aureus* (1.5-3.12 μg/ml). In addition, the incorporated vancomycin was totally released within one day of the in vitro immersion study. This is not a satisfactory release profile.

None of the applications described by these authors are relate to the thin films on substrates incorporating controlled release of pharmaceutically active compounds and none of the disclosed techniques are suitable for providing them. The presence of these pharmaceutically active compounds affects the synthesis and the properties of the resulting films. Critical properties are the film stability in biological milieus, molecular release kinetics and mechanical adherence of the coating to the substrate. None of these issues were addressed previously.

What is claimed is:

1. Biocompatible composite comprising:
   substrate and, on the substrate;
   xerogel film of thickness from 0.05 μm to about 10 μm;
      the xerogel containing at least one biologically functional pharmaceutically active compound;
      the xerogel being formed, without a sintering step, from a sol-gel layer containing the pharmaceutically active compound.

2. The composite of claim 1 wherein the thickness of the xerogel is from 0.3 to about 2 μm.

3. The composite of claim 1 wherein the thickness of the xerogel is from 0.5 to about 1.5 μm.

4. The composite of claim 1 wherein the sol-gel is formed from silicon alkoxide.

5. The composite of claim 1 wherein the sol-gel is formed from silicon alkoxide in a medium miscible with water.

6. The composite of claim 1 wherein the sol-gel is formed from silicon alkoxide and the pharmaceutically active compound is water miscible.

7. The composite of claim 4 wherein the sol gel-also comprises additional oxide.

8. The composite of claim 4 wherein the sol-gel further comprises at least one of calcium oxide and phosphorous pentoxide.

9. The composite of claim 6 wherein the sol-gel results from a liquid sol at least partially formed at acid pH.

10. The composite of claim 1 wherein the xerogel film has a porosity of less than about 20 percent.

11. The composite of claim 1 wherein the xerogel film has a porosity of less than about 15 percent.

12. The composite of claim 1 wherein the xerogel film has a porosity of less than about 10 percent.

13. The composite of claim 1 wherein the xerogel film has a specific surface area of less than about 200 m2/g.

14. The composite of claim 1 wherein the xerogel film has a specific surface area of less than about 150 m2/g.

15. The composite of claim 1 wherein the xerogel film has a porosity of less than about 10 percent and a specific surface area of less than about 150 m2/g.

16. The composite of claim 1 wherein the pharmaceutically active compound is antibiotic, antineoplastic, antiangiogenic, antithrombogenic, anti-inflammatory, analgesic, a cytokine or a tissue growth stimulating moiety.

17. The composite of claim 1 wherein the pharmaceutically active compound is a vancomycin.

18. The composite of claim 1 wherein the pharmaceutically active compound is bipuvacaine or another analgesic.

19. The composite of claim 1 wherein, included in the sol-gel are particles of a second sol-gel, at least one of the sol-gel layer or particles containing the pharmaceutically active compound.

20. A biocompatible implant comprising the biocompatible composite according to claim 1 wherein the implant releases the pharmaceutically active compound in therapeutically effective amounts over a preselected period of time between about 1 day and about 12 months when placed into contact with a bodily fluid.

21. The implant of claim 20 wherein the thickness of the xerogel is from 0.3 to about 2 μm.

22. The implant of claim 20 wherein the thickness of the xerogel is from 0.5 to about 1.5 μm.

23. The implant of claim 20 wherein the sol-gel is formed from silicon alkoxide.

24. The implant of claim 20 wherein the sol-gel is formed from silicon alkoxide in water miscible medium.

25. The implant of claim 20 wherein the sol-gel is formed from silicon alkoxide and the pharmaceutically active compound is water miscible.

26. The implant of claim 22 wherein the sol-gel also comprises additional oxide.

27. The implant of claim 22 wherein the sol-gel further comprises at least one of calcium oxide and phosphorous pentoxide.

28. The implant of claim 22 wherein the sol-gel results from a liquid sol at least partially formed at acid pH.

29. The implant of claim 20 wherein the xerogel film has a porosity of less than about 20 percent.

30. The implant of claim 20 wherein the xerogel film has a porosity of less than about 15 percent.

31. The implant of claim 20 wherein the xerogel film has a porosity of less than about 10 percent.

32. The implant of claim 20 wherein the xerogel film has a specific surface area of less than about 200 m2/g.

33. The implant of claim 20 wherein the xerogel film has a specific surface area of less than about 150 m2/g.

34. The implant of claim 20 wherein the xerogel film has a porosity of less than about 10 percent and a specific surface area of less than about 150 m2/g.

35. The implant of claim 20 wherein the pharmaceutically active compound is antibiotic, antineoplastic, antiangiogenic, antithrombogenic, anti-inflammatory, analgesic, a cytokine or a tissue growth stimulating moiety.

36. The implant of claim 20 wherein the pharmaceutically active compound is a vancomycin.

37. The implant of claim 20 wherein the pharmaceutically active compound is bipuvacaine or another analgesic.

38. The implant of claim 20 wherein, included in the sol-gel are particles of a second sol-gel, at least one of the sol-gel layer or particles containing the pharmaceutically active compound.

39. The implant of claim 20 comprising a plurality of xerogel films.

40. The composite according to claim 1 wherein said xerogel film comprises at least one additional xerogel layer on said first xerogel film.

41. The composite according to claim 40 wherein said biocompatible composite comprises one additional xerogel layer on said xerogel film.

42. The composite according to claim 40 wherein said biocompatible composite comprises two additional xerogel layers on said xerogel film.

43. The composite according to claim 40 wherein each of said at least one additional xerogel layers contains at least one biologically functional pharmaceutically active compound.

44. The composite according to claim 43 wherein said at least one pharmaceutically active compound in said additional xerogel layers is the same as said at least one pharmaceutically active compound in said xerogel film.

45. The composite according to claim 40 wherein said at least one pharmaceutically active compound is present in said biocompatible composite in an amount sufficient to provide a therapeutic dose of said at least one pharmaceutically active compound.

46. The composite according to claim 1 wherein said at least one pharmaceutically active compound is present in said biocompatible composite in an amount sufficient to provide a therapeutic dose of said at least one pharmaceutically active compound.

* * * * *